(12) United States Patent
Timoszyk et al.

(10) Patent No.: US 9,945,498 B2
(45) Date of Patent: Apr. 17, 2018

(54) MULTI-STAGE ROTARY OVERTRAVEL STOP

(71) Applicants: Wojciech K. Timoszyk, Flower Mound, TX (US); James Dulin Reavill, Irving, TX (US)

(72) Inventors: Wojciech K. Timoszyk, Flower Mound, TX (US); James Dulin Reavill, Irving, TX (US)

(73) Assignee: STRYKER CORPORATION, Kalamazoo, MI (US)

( * ) Notice: Subject to any disclaimer, the term of this patent is extended or adjusted under 35 U.S.C. 154(b) by 657 days.

(21) Appl. No.: 14/580,401

(22) Filed: Dec. 23, 2014

(65) Prior Publication Data

US 2015/0184779 A1     Jul. 2, 2015

Related U.S. Application Data

(60) Provisional application No. 61/921,160, filed on Dec. 27, 2013.

(51) Int. Cl.
    *A61B 90/30*     (2016.01)
    *F16L 3/01*     (2006.01)

(52) U.S. Cl.
    CPC .............. *F16L 3/01* (2013.01); *A61B 90/30* (2016.02); *A61B 2090/308* (2016.02)

(58) Field of Classification Search
    CPC ..... Y10T 403/32975; Y10T 403/32213; Y10T 403/32549
    See application file for complete search history.

(56) References Cited

U.S. PATENT DOCUMENTS

| | | | | |
|---|---|---|---|---|
| 1,551,332 A | * | 8/1925 | Schramm | F16M 11/2007 285/181 |
| 3,305,294 A | | 2/1967 | Alvarez | |
| 4,009,731 A | * | 3/1977 | Denz | E03C 1/0404 138/155 |
| 4,726,552 A | * | 2/1988 | Warshawsky | F21S 6/002 248/122.1 |
| 4,880,193 A | * | 11/1989 | Warshawsky | F21S 6/003 248/122.1 |
| 5,128,848 A | | 7/1992 | Enders et al. | |
| 5,253,832 A | | 10/1993 | Bolas et al. | |
| 5,400,993 A | | 3/1995 | Hamilton | |

(Continued)

OTHER PUBLICATIONS

Stryker Communications "Flexible Solutions for Critical Care" brochure; Copyright 2011.

(Continued)

*Primary Examiner* — Daniel J Wiley
(74) *Attorney, Agent, or Firm* — Flynn, Thiel, Boutell & Tanis, P.C.

(57) ABSTRACT

A medical device assembly including a first member having a first abutment, a second member rotatably connected to the first member and having a second abutment, and an idler member having third abutment and a fourth abutment. The first member is rotatably fixed to the second member. The idler member is free to rotate relative to the first member and the second member until the first abutment abuts the third abutment and until the second abutment abuts the fourth abutment. The first member, the second member and the idler member all rotate relative to each other about a single axis.

28 Claims, 10 Drawing Sheets

(56) References Cited

U.S. PATENT DOCUMENTS

| | | | |
|---|---|---|---|
| 5,685,661 A * | 11/1997 | Marka | F16C 11/04 403/112 |
| 5,803,905 A | 9/1998 | Allred et al. | |
| 5,820,253 A | 10/1998 | Scholz | |
| 6,250,774 B1 | 6/2001 | Begemann et al. | |
| 6,402,351 B1 | 6/2002 | Borders et al. | |
| 6,434,329 B1 | 8/2002 | Dube et al. | |
| 6,464,383 B1 | 10/2002 | Northington et al. | |
| 6,471,363 B1 | 10/2002 | Howell et al. | |
| 6,522,529 B1 | 2/2003 | Huilgol et al. | |
| 6,581,887 B2 | 6/2003 | Lapidez | |
| 6,601,811 B1 | 8/2003 | Van Lieshout | |
| 6,644,837 B2 | 11/2003 | Borders et al. | |
| 6,692,141 B2 | 2/2004 | Jesurun et al. | |
| 6,863,417 B2 | 3/2005 | Hill | |
| 6,863,422 B2 | 3/2005 | Jesurun et al. | |
| 6,896,233 B2 | 5/2005 | Kuhn | |
| 6,899,442 B2 | 5/2005 | Howell et al. | |
| 7,210,662 B2 | 5/2007 | Liou et al. | |
| 7,369,672 B2 * | 5/2008 | Hirschhorn | F16M 11/041 248/917 |
| 7,701,151 B2 | 4/2010 | Petrucci et al. | |
| 7,793,907 B2 | 9/2010 | Woodward et al. | |
| 7,812,551 B2 | 10/2010 | Hite et al. | |
| 7,857,619 B2 | 12/2010 | Liu | |
| RE42,091 E | 2/2011 | Moscovitch et al. | |
| 7,990,078 B2 | 8/2011 | Petrucci et al. | |
| 8,172,751 B2 | 5/2012 | Kusner et al. | |
| 8,226,419 B2 * | 7/2012 | Fonzo | H01R 35/02 439/11 |
| RE44,727 E | 1/2014 | Bosson | |
| 8,771,182 B2 | 7/2014 | Kusner et al. | |
| 2006/0039160 A1 | 2/2006 | Cassarly et al. | |
| 2009/0226131 A1 | 9/2009 | Zhang et al. | |
| 2010/0053982 A1 | 3/2010 | Klaus et al. | |
| 2013/0053741 A1 * | 2/2013 | Pittaccio | A61F 5/0102 602/16 |
| 2013/0100687 A1 * | 4/2013 | Chen | F21S 8/06 362/427 |
| 2013/0258661 A1 | 10/2013 | Jousse et al. | |

OTHER PUBLICATIONS

Stryker Communications "Providing Efficiency with Flexible Solutions" brochure; Copyright 2011.

\* cited by examiner

MULTI-STAGE ROTARY OVERTRAVEL STOP

CROSS REFERENCE TO RELATED APPLICATION

This application claims the benefit of U.S. Provisional Application Ser. No. 61/921,160, filed Dec. 27, 2013.

FIELD OF THE INVENTION

The present invention relates to a joint, and in particular to a stop for a rotary joint that can be used in medical devices.

BACKGROUND OF THE INVENTION

Surgical lights have been used in operating rooms to provide increased light to a specific area of the room. Likewise, other wired devices, such as monitors, speakers, joysticks, keyboards and cameras, have been used in operating rooms to provide surgical information to a surgeon or other person in the operating room (e.g., images from a camera or patient vital information). Moreover, booms holding IVs, shelves, electrical outlets and/or gas outlets are used to assist medical personnel in helping patients. Such apparatuses receive and/or provide signals and power and/or gas to and/or from various supports mounted or provided in the operating room, thereby requiring conduits (including cables (e.g., electrical power, electrical data and fiber optic) and/or gas hoses) to extend through supports for such devices to the devices.

SUMMARY OF THE INVENTION

The present invention, according to one aspect, is directed to a rotary joint for use in a medical application including a first linkage having a first abutment, a second linkage rotatably connected to the first linkage, with the second linkage having a second abutment, and an idler member having a third abutment at a top side thereof and a fourth abutment at a bottom side thereof. At least one conduit extends through the first linkage and the second linkage. The first linkage has at least one connector being rotatably fixed to the second linkage for allowing the first linkage to rotate relative to the second linkage. The idler member is free to rotate relative to the first linkage and the second linkage until the first abutment of the first linkage abuts the third abutment of the idler member and until the second abutment of the second linkage abuts the fourth abutment of the idler member. The first linkage is able to rotate relative to the second linkage at a maximum angular displacement that is greater than 360°. The first linkage, the second linkage and the idler member all rotate relative to each other about a single axis.

Another aspect of the present invention includes providing a medical device assembly including a first member having a first abutment, a second member rotatably connected to the first member, with the second member having a second abutment, and an idler member having a third abutment at a top side thereof and a fourth abutment at a bottom side thereof. At least one conduit extends through the first member and the second member. The first member is rotatably fixed to the second member. The idler member is free to rotate relative to the first member and the second member until the first abutment of the first member abuts the third abutment of the idler member and until the second abutment of the second member abuts the fourth abutment of the idler member. The first member, the second member and the idler member all rotate relative to each other about a single axis.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements.

Figure 1:
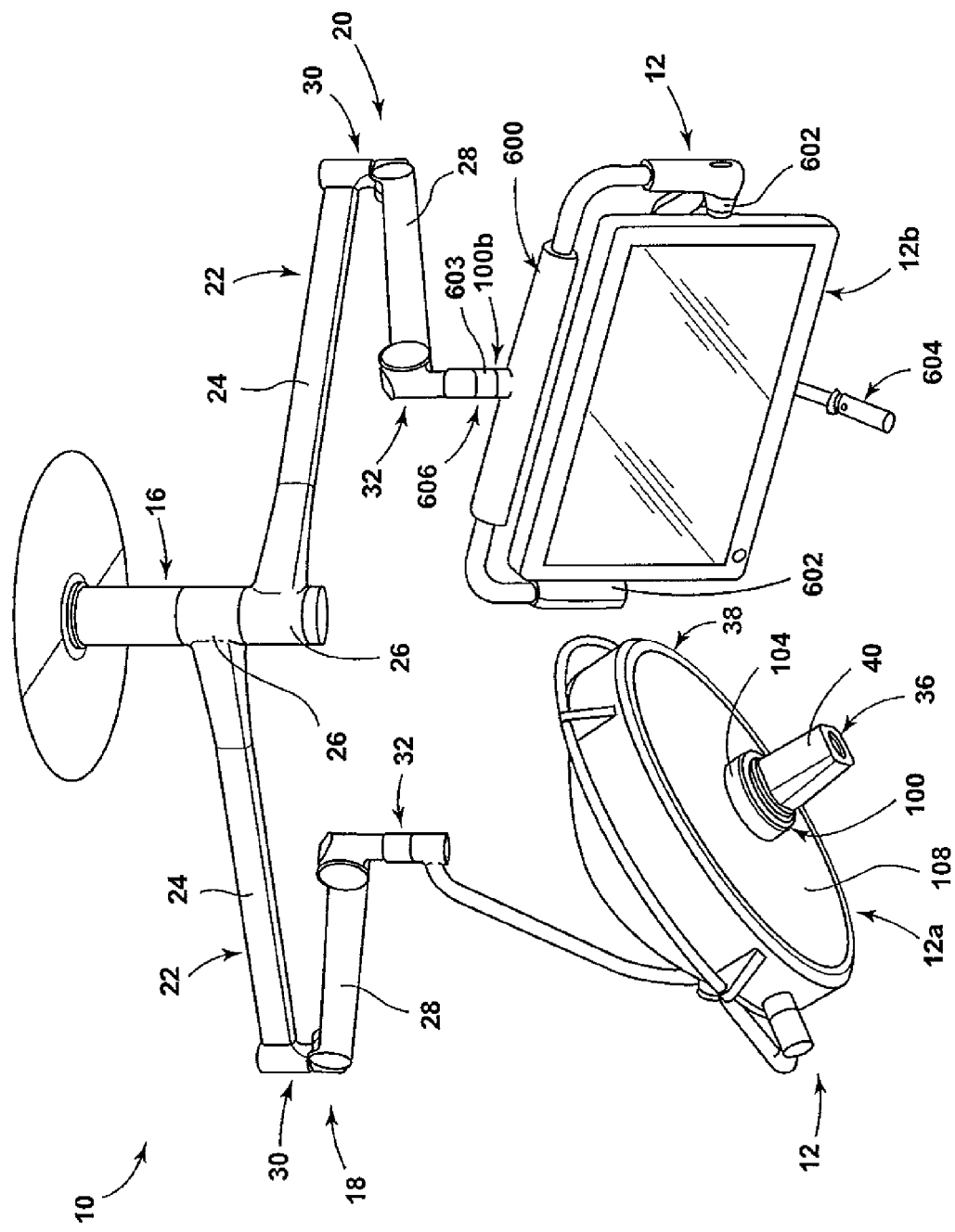
FIG. 1 illustrates a perspective view of a medical device assembly according to the invention.

The specific devices and processes illustrated in the attached drawings, and described in the following specification are simply exemplary embodiments of the inventive concepts. Hence, specific dimensions and other physical characteristics relating to the embodiments disclosed herein are not to be considered as limiting.

DETAILED DESCRIPTION

The reference number 10 (FIG. 1) generally designates a medical device assembly of the present invention. The medical device assembly 10 is configured to be positioned within a room (e.g., operating room) and includes at least one wired medical unit 12 configured to provide information to the medical personnel in the room and/or assist the medical personnel in the room perform various functions. In the illustrated example, the medical device assembly 10 includes a plurality of wired medical units 12 in the form of a surgical light 12a configured to provide increased light to a specific area of the room and a monitor 12b for providing surgical information to a surgeon or other person in the operating room (e.g., images from a camera or patient vital information).

The illustrated surgical light 12a is connected to a ceiling attachment bracket 16 by a first arm assembly 18 and the monitor 12b is connected to the ceiling attachment bracket 16 by a second arm assembly 20. It is contemplated that the medical device assembly 10 can include any number of arm assemblies and wired medical units 12, including only one arm assembly and wired medical unit 12, and that each arm assembly can include a plurality of wired medical units 12 supported therefrom. While the medical device assembly 10 is illustrated as being connected to a ceiling, the medical device assembly 10 can be directly connected to a suspension system connected to a wall or ceiling of the operating room, can be connected to a further arm assembly (not shown) directly connected to a wall or ceiling of the operating room, or can be directly or indirectly connected to a movable assembly located within the operating room.

In the illustrated example, the first arm assembly 18 and the second arm assembly 20 can be selectively moved and positioned to allow for a person to position the wired medical units 12 in a desired location. The illustrated first arm assembly 18 and the second arm assembly 20 each include a plurality of arms 22 and joints for adjusting a position of the medical units 12. For example, the first arm assembly 18 and the second arm assembly 20 can each include a first arm 24 connected to the ceiling attachment bracket 16 by a shoulder joint 26 and a second arm 28 connected to the first arm 24 by an elbow joint 30, with the medical unit 12 being connected to the second arm 28 by a wrist joint 32. At least one conduit 34 extends through the ceiling attachment bracket 16, the shoulder joint 26, the first arm 24, the elbow joint 30, the second arm 28 and the wrist joint 32 to the medical units 12 to provide and/or receive signals and power to and/or from the medical units 12. In the illustrated example, the at least one conduit is electrical wiring.

In order to allow a full range of motion of the first arm assembly 18 and the second arm assembly 20 so that the wired medical units 12 can be selectively located or positioned, the wired medical units 12 have several joints 26, 30, 32. In order to prevent potentially damaging twisting of the at least one conduit 34 within the arm assemblies 18, 20 and the wired medical units 12, several of the joints of the medical device assembly 10 can each include a rotary joint 100 with a multi-stage rotary overtravel stop to prevent unlimited rotation of the joints having the at least one conduit 34 extending therethrough. Furthermore, portions of the medical units 12 can have the rotary joint 100 with the multi-stage rotary overtravel stop to prevent unlimited rotation of the joints to thereby prevent potentially damaging twisting of the at least one conduit 34.

Figure 2:
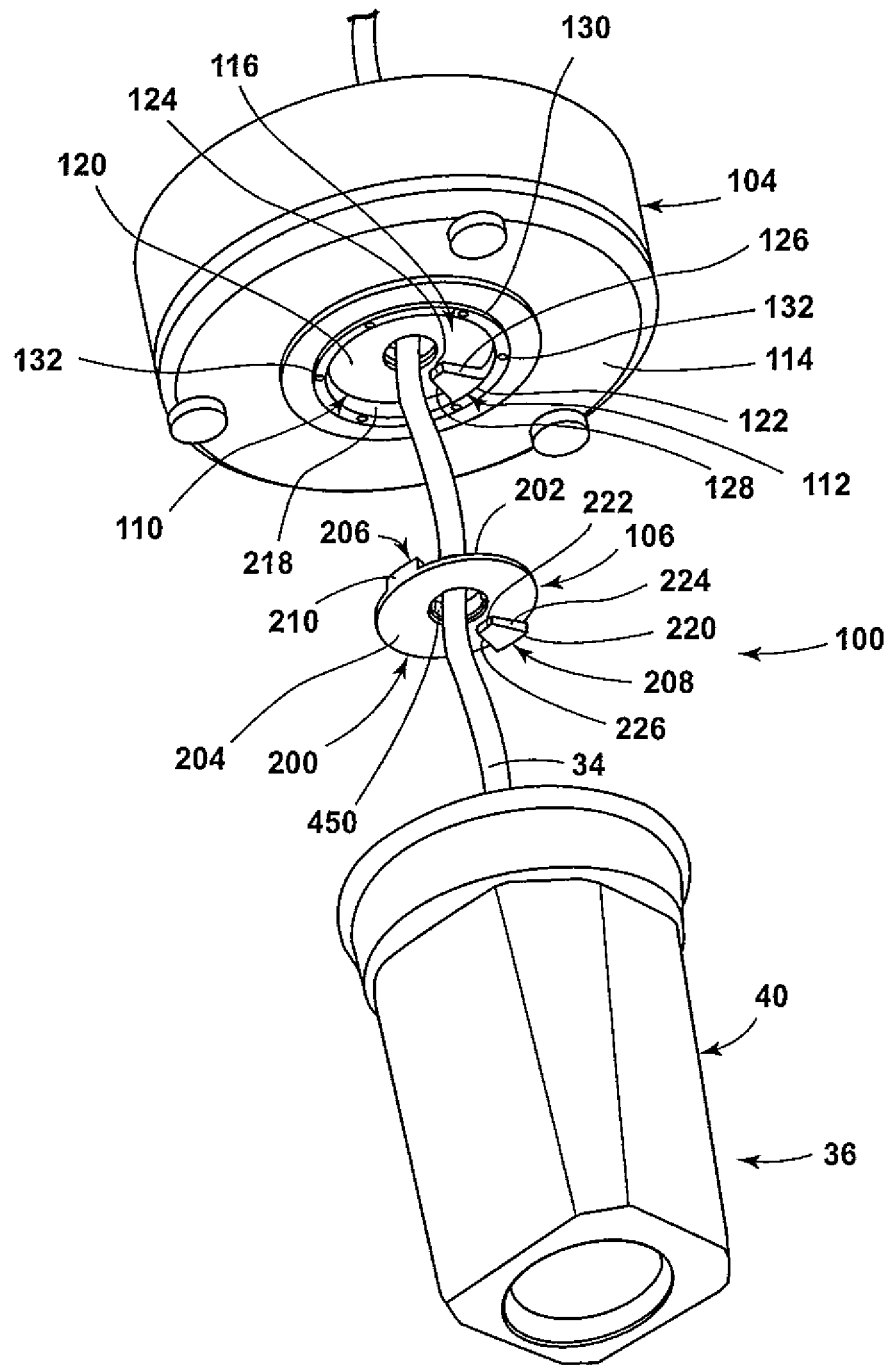
FIG. 2 is a first exploded perspective view of a surgical light camera having a first rotary joint with a multi-stage rotary overtravel stop according to the invention.
Figure 3:
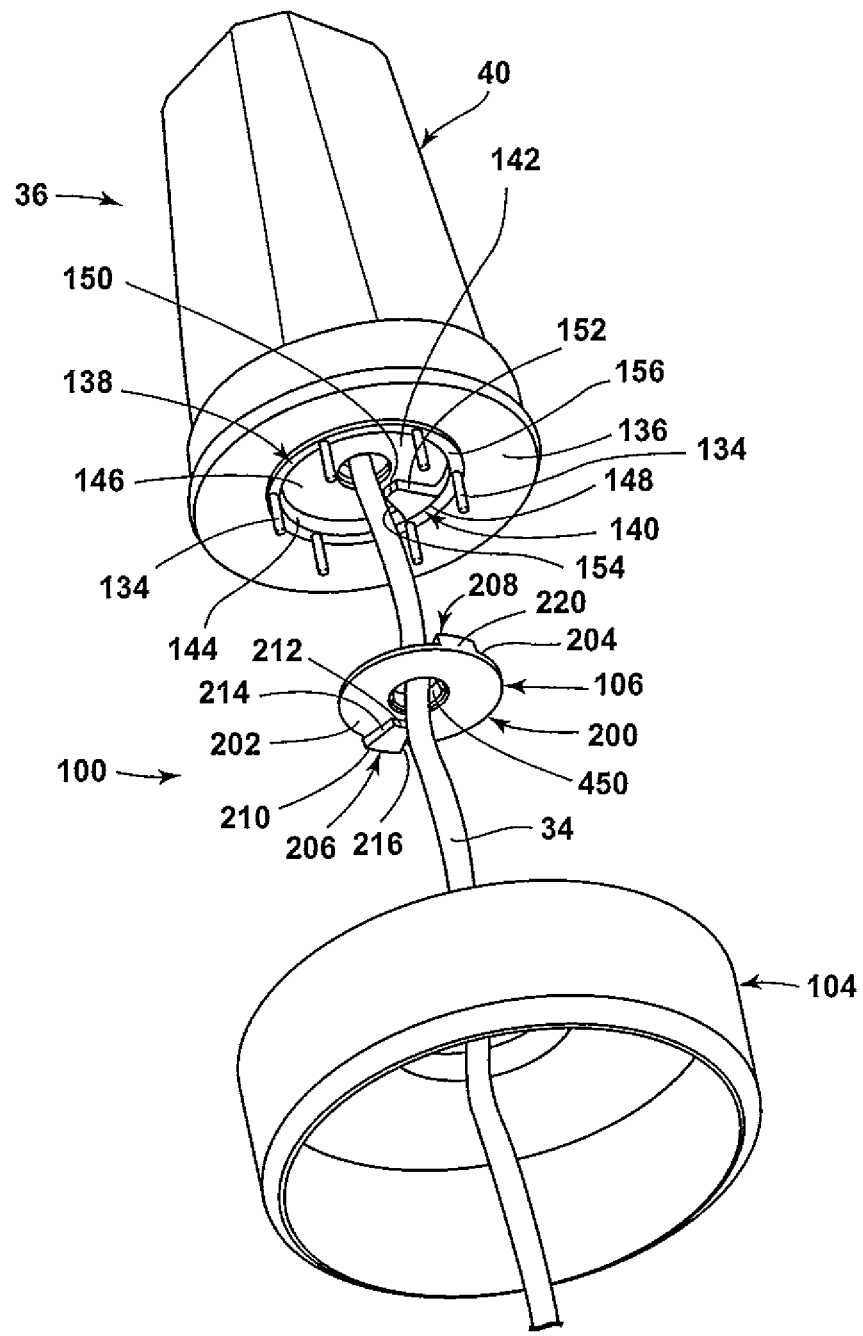
FIG. 3 is a second exploded perspective view of the surgical light camera having the first rotary joint with a multi-stage rotary overtravel stop according to the invention, with FIG. 3 being inverted relative to the position of the surgical light camera having the first rotary joint shown in FIG. 2.

FIGS. 1-3 illustrate a first embodiment of the rotary joint 100 with a multi-stage rotary overtravel stop for use with the illustrated surgical light 12a. In the illustrated example, the surgical light 12a can include a surgical camera assembly 36 having a camera housing 40 rotatably connected to a light housing 38 of the surgical light 12a. Surgical camera assemblies 36 for use with surgical lights 12a are well known to those skilled in the art. As illustrated in FIGS. 1-3, the surgical camera assembly 36 is connected to the light housing 38 using the rotary joint 100. The rotary joint 100 with the multi-stage rotary overtravel stop limits the rotation of the surgical camera assembly 36 relative to the light housing 38 (e.g., to a range of motion greater than 360°) to thereby prevent potentially damaging twisting of the at least one conduit 34.

The rotary joint 100 as illustrated in FIGS. 1-3 includes a first member in the form of a bezel 104 connected to the light housing 38 of the surgical light 12a, a second member in the form of the camera housing 40 and an idler member 106. The bezel 104 is annular or disc-shaped and extends outwardly from a light emitting area 108 of the surgical light 12a. The bezel 104 has a front face 114 including a first abutment area 110 having a first abutment 112 for limiting or stopping rotation of the idler member 106. The first abutment area 110 includes a first circular recess 116 defined by an outer cylindrical wall 118 and a flat bottom wall 120 oriented transversely to one another. The first abutment 112 is located within the first circular recess 116 and extends inwardly from the outer cylindrical wall 118 and the downwardly from flat bottom wall 120 as illustrated in FIG. 2. The first abutment 112 is substantially trapezoidal having a radially outward longest edge 122 connected to the outer cylindrical wall 118 of the first circular recess 116, a radially inward smallest edge 124 opposite the longest edge 122, a first abutment first contact edge 126 and a second abutment second contact edge 128. As illustrated in FIG. 2, the first circular recess 116 is surrounded by an outer rotary cylindrical ridge 130 defining the outer cylindrical wall 118. The ridge 130 has a plurality of openings 132 therein configured to receive post-like projections 134 extending outwardly from the camera housing 40 to connect the camera housing 40 to the bezel 104.

The illustrated camera housing 40 engages with the bezel 104 so as to rotate relative thereto. The camera housing 40 has a bottom face 136 including a second abutment area 138 with a second abutment 140 for limiting or stopping rotation of the idler member 106. The second abutment area 138 includes a second circular recess 142 defined by an outer cylindrical wall 144 and a flat bottom wall 146 oriented transversely to one another. The second abutment 140 is located within the second circular recess 142 and extends inwardly from the outer cylindrical wall 144 and outwardly from the flat bottom wall 146. The second abutment 140 is substantially trapezoidal having a radially outward longest edge 148 connected to the outer cylindrical wall 144 of the second circular recess 142, a radially inward smallest edge 150 opposite the longest edge 148, a second abutment first contact edge 152 and a second abutment second contact edge 154. As illustrated in FIG. 3, the second circular recess 142 is surrounded by an outer rotary cylindrical ridge 156 defining the outer cylindrical wall 144. The ridge 156 has the post-like projections 134 extending outwardly therefrom. The projections 134 extend into the openings 132 in the outer rotary cylindrical ridge 130 of the bezel 104. The outer rotary cylindrical ridge 130 of the bezel 104 rotates freely relative to the outer cylindrical ridge 156 of the camera housing 40 to allow the camera housing 40 to freely rotate relative to the bezel 104.

In the illustrated example, the idler member 106 is captured between the bezel 104 and the camera assembly 36 to limit rotation of the camera housing 40 of the camera assembly 36 relative to the bezel 104 and the light housing 38. The idler member 106 includes a disc 200 having a top surface 202 and an oppositely facing bottom surface 204. A third abutment 206 extends axially from the top surface 202 and a fourth abutment 208 extends axially from the bottom surface 204. The third abutment 206 is similar in configuration to the first abutment 112, and is substantially trapezoidal having a peripheral longest edge 210, a radially inward smallest edge 212 opposite the longest edge 210, a third abutment first contact edge 214 and a third abutment second contact edge 216. The fourth abutment 208 is substantially trapezoidal having a peripheral longest edge 220, a radially inward smallest edge 222 opposite the longest edge 220, a fourth abutment first contact edge 224 and a fourth abutment second contact edge 226.

Figure 4:
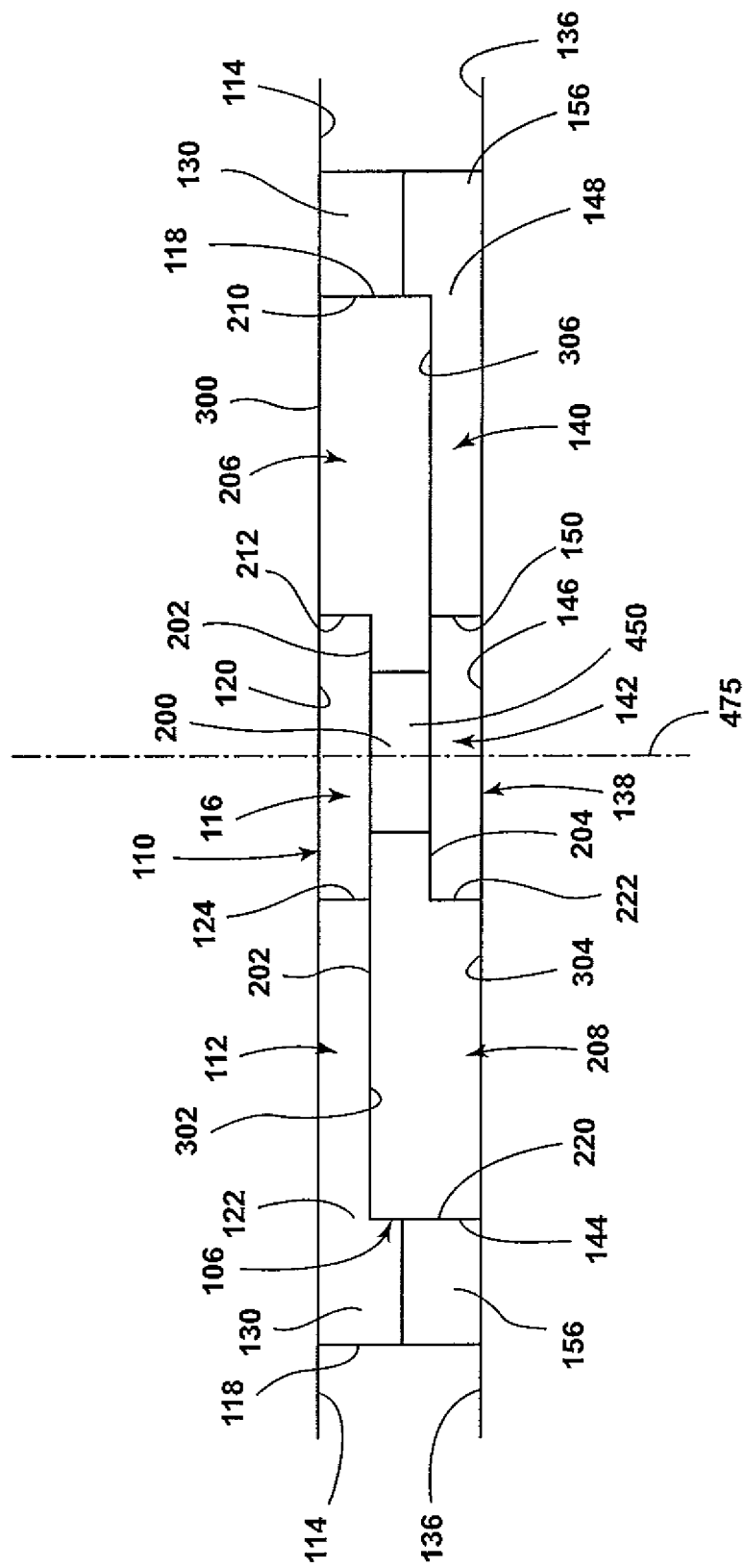
FIG. 4 is a cross-sectional view of an idler member, the first abutment area and the second abutment area of the first rotary joint with a multi-stage rotary overtravel stop according to the invention.

The illustrated idler member 106 is captured between the bezel 104 and the camera assembly 36. FIG. 4 illustrates a cross-sectional view of the idler member 106, the first abutment area 110 and the second abutment area 138 (along with illustrating the outer rotary cylindrical ridge 130 of the bezel 104 and the outer rotary cylindrical ridge 156 of the camera housing 40). As illustrated in FIG. 4, the third abutment 206 is located in the first circular recess 116 of the first abutment area 110, with a top surface 300 of the third abutment 206 abutting and riding on the flat bottom wall 120 of the first circular recess 116. Likewise, a bottom surface 302 of the first abutment 112 rides on the top surface 202 of the disc 200 of the idler member 106. Furthermore, the fourth abutment 208 is located in the second circular recess 142 of the second abutment area 138, with a bottom surface 304 of the fourth abutment 208 abutting and riding on the flat bottom wall 146 of the second circular recess 142. Likewise, a top surface 306 of the first abutment 140 rides on the bottom surface 204 of the disc 200 of the idler member 106.

Figure 5:
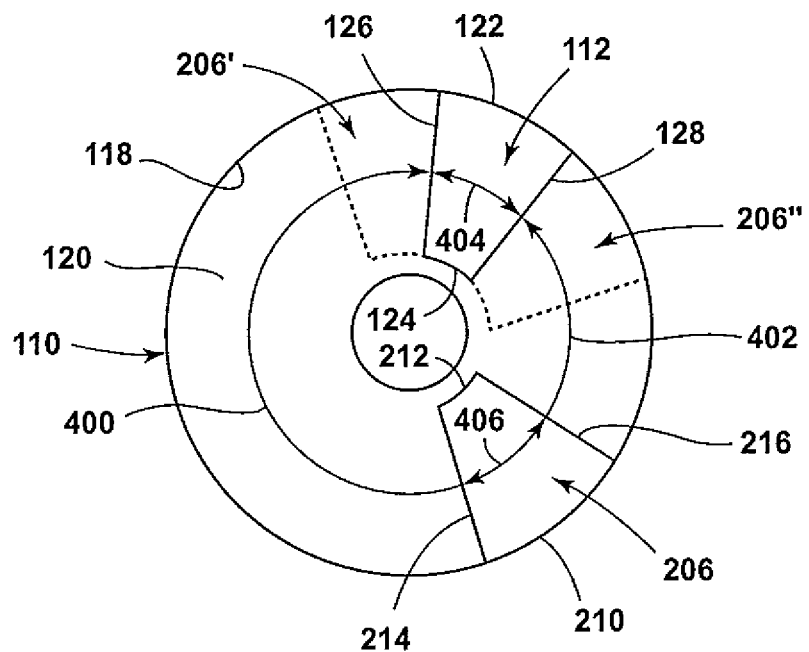
FIG. 5 illustrates a range of motion of the idler member relative to a bezel of the first rotary joint with a multi-stage rotary overtravel stop according to the invention.

FIG. 5 illustrates the range of motion of the idler member 106 relative to the bezel 104. FIG. 5 is a top view of the first abutment area 110 with the flat bottom wall 120, the outer cylindrical wall 118 and the first abutment 112. The third abutment 206 moves about a center of the first abutment area 110 within the first circular recess 116 of the first abutment area 110. As illustrated in FIG. 5, the third abutment 206 can move clockwise along line 400 until the third abutment first contact edge 214 of the third abutment 206 abuts against the first abutment first contact edge 126 (in position 206' as shown in dotted lines), thereby preventing further rotation of the third abutment 206. Likewise, the third abutment 206 can move counter-clockwise along line 402 until the third abutment second contact edge 216 of the third abutment 206 abuts against the second abutment second contact edge 128 (in position 206" as shown in dotted lines), thereby preventing further rotation of the third abutment 206. A maximum angular distance of rotation the third abutment 206 within the first circular recess 116 of the first abutment area 110 of the bezel 104 is equal to 360° minus a first angular width 404 (in degrees) of the first abutment 112 and minus a third angular width 406 (in degrees) of the third abutment 206.

Figure 6:
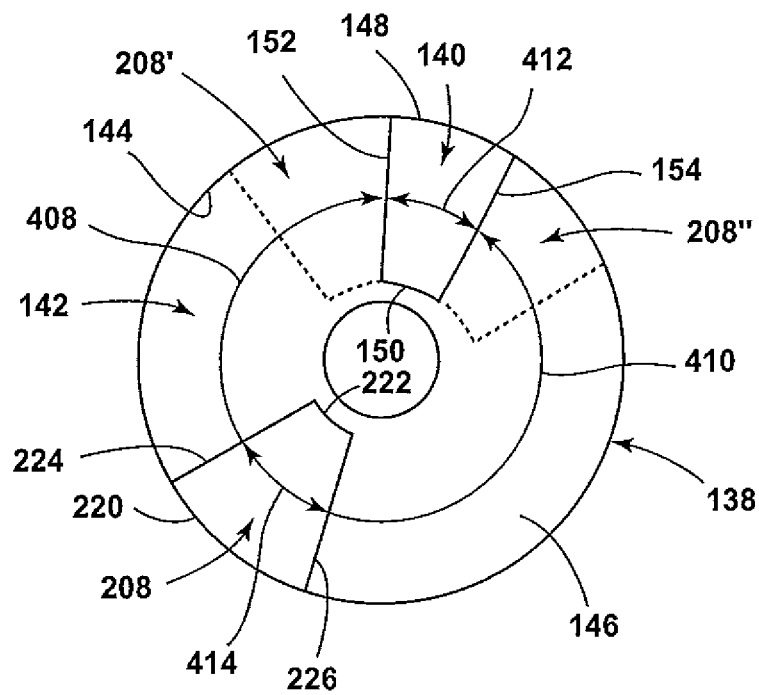
FIG. 6 illustrates a range of motion of the idler member relative to a light housing of the first rotary joint with a multi-stage rotary overtravel stop according to the invention.

FIG. 6 illustrates the range of motion of the idler member 106 relative to the camera assembly 36. FIG. 6 shows a bottom view of the second abutment area 138 with the flat bottom wall 146, the outer cylindrical wall 144 and the second abutment 140. The fourth abutment 208 moves about a center of the second abutment area 138 within the second circular recess 142 of the second abutment area 138. As illustrated in FIG. 6, the fourth abutment 208 can move clockwise along line 408 until the fourth abutment first contact edge 224 of the fourth abutment 208 abuts against the second abutment first contact edge 152 (in position 208' as shown in dotted lines), thereby preventing further rotation of the fourth abutment 208. Likewise, the forth abutment 208 can move counter-clockwise along line 410 until the fourth abutment second contact edge 226 of the fourth abutment 208 abuts against the second abutment second contact edge 154 (in position 208" as shown in dotted lines), thereby preventing further rotation of the fourth abutment 208. A maximum angular distance of rotation the fourth abutment 208 within the second circular recess 142 of the second abutment area 138 of the camera assembly 36 is equal to 360° minus a second angular width 412 (in degrees) of the second abutment 140 and minus a fourth angular width 414 (in degrees) of the fourth abutment 208.

Figure 4A:
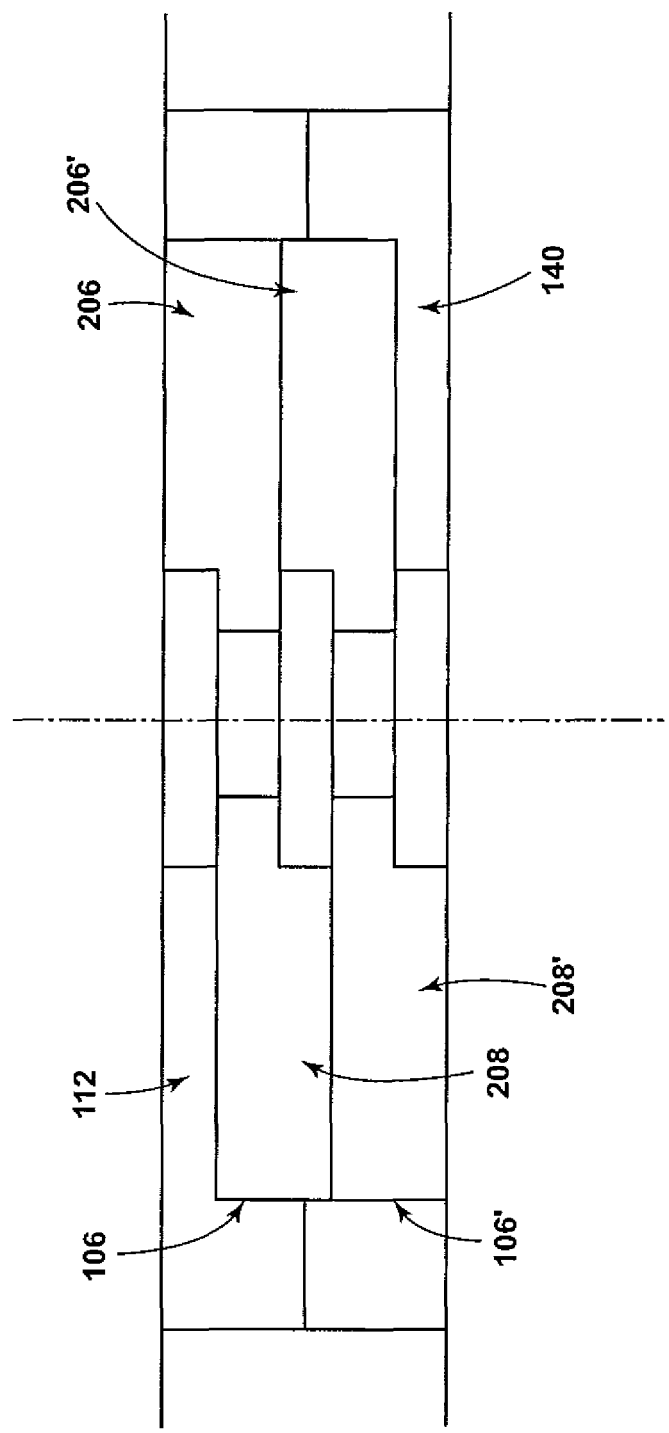
FIG. 4A is a cross-sectional view of the first rotary joint with a multi-stage rotary overtravel stop according to the invention having multiple idler members.

In the illustrated embodiment, the idler member 106 allows the camera assembly 36 to rotate relative to the light housing 38 greater than 360° to allow for a wide range of angles, but not more than 720° to prevent unlimited rotation of the camera assembly 36 to thereby prevent potentially damaging twisting to the at least one conduit 34 leading from the light housing 38 to the camera assembly 36. The maximum angular distance of rotation of the camera assembly 36 relative to the light housing 38 is 720° minus the first angular width 404 (in degrees) of the first abutment 112, the second angular width 412 (in degrees) of the second abutment 140, the third angular width 406 (in degrees) of the third abutment 206, and the fourth angular width 414 (in degrees) of the fourth abutment 208. Accordingly, the maximum angular distance of rotation of the camera assembly 36 relative to the light housing 38 can be adjusted by altering the angular widths of the first abutment 112, the second abutment 140, the third abutment 206 and/or the fourth abutment 208. It is also contemplated that multiple idler members 106, 106' (with abutments 206' and 208') could be used (see FIG. 4A), with the maximum angular distance of rotation of the camera assembly 36 relative to the light housing 38 being calculated as 360° plus 360° times the number of idler members 106 minus the angular widths of all of the abutments.

The illustrated idler member 106 is free to rotate relative to the camera assembly 36 and the light housing 38. In the illustrated embodiment, the camera assembly 36, the light housing 38 and the idler member 106 rotate relative to each other about a single axis 475 (see FIG. 4). Moreover, the idler member 106 is maintained in position within the first circular recess 116 of the first abutment area 110 and the second circular recess 142 of the second abutment area 138 through engagement with the first abutment 112, the flat bottom wall 120, and the outer cylindrical wall 118 of the first abutment area 110 and the second abutment 140, the flat bottom wall 146, and the outer cylindrical wall 144 of the second abutment area 138. However, it is contemplated that the idler member 106 could be maintained in position within the first circular recess 116 of the first abutment area 110 and the second circular recess 142 of the second abutment area 138 through additional structures. For example, a post (not shown) could extend from the camera assembly 36 and/or the bezel 104 of the light housing 38 through a center opening 450 in the disc 200 of the idler member 106. The post could maintain the idler member 106 is a set axial and/or radial position, but allow the idler member 106 to freely rotate about the post.

While an illustrated bezel 104, idler member 106 and camera assembly 36 are shown, the bezel 104, idler member 106 and camera assembly 36 could have other configurations. For example, while the abutments are shown and illustrated as being substantially trapezoidal, the abutments could have other shapes. In this regard, each abutment could include a pair of walls or pillars that form each abutment edge for each abutment. Each abutment could also be rectangular, circular or take any other shape. The angular widths in degrees of the abutments in any form is the angular distance wherein an abutment on the idler member 106 cannot travel within one of the circular recesses. In the illustrated example, the at least one conduit 34 extends through the center opening 450 in the disc 200 of the idler member 106 (and could extend through any post through the center opening 450). However, it is contemplated that the at least one conduit 34 could extend between the camera assembly 36 and the light housing 38 outside of the idler member 106.

The reference numeral 106a (FIGS. 7-8) generally designates another embodiment of the present invention, which includes a second embodiment for the idler member. The second embodiment of the idler member 106a includes a damping member in the form of springs to damp impact of the abutments. The second embodiment of the idler member 106a includes a disc 200a having a top surface 202a and an oppositely facing bottom surface 204a. A third abutment 206a extends axially outwardly from the top surface 202a and a fourth abutment 208a extends axially outwardly from the bottom surface 204a.

Figure 7:
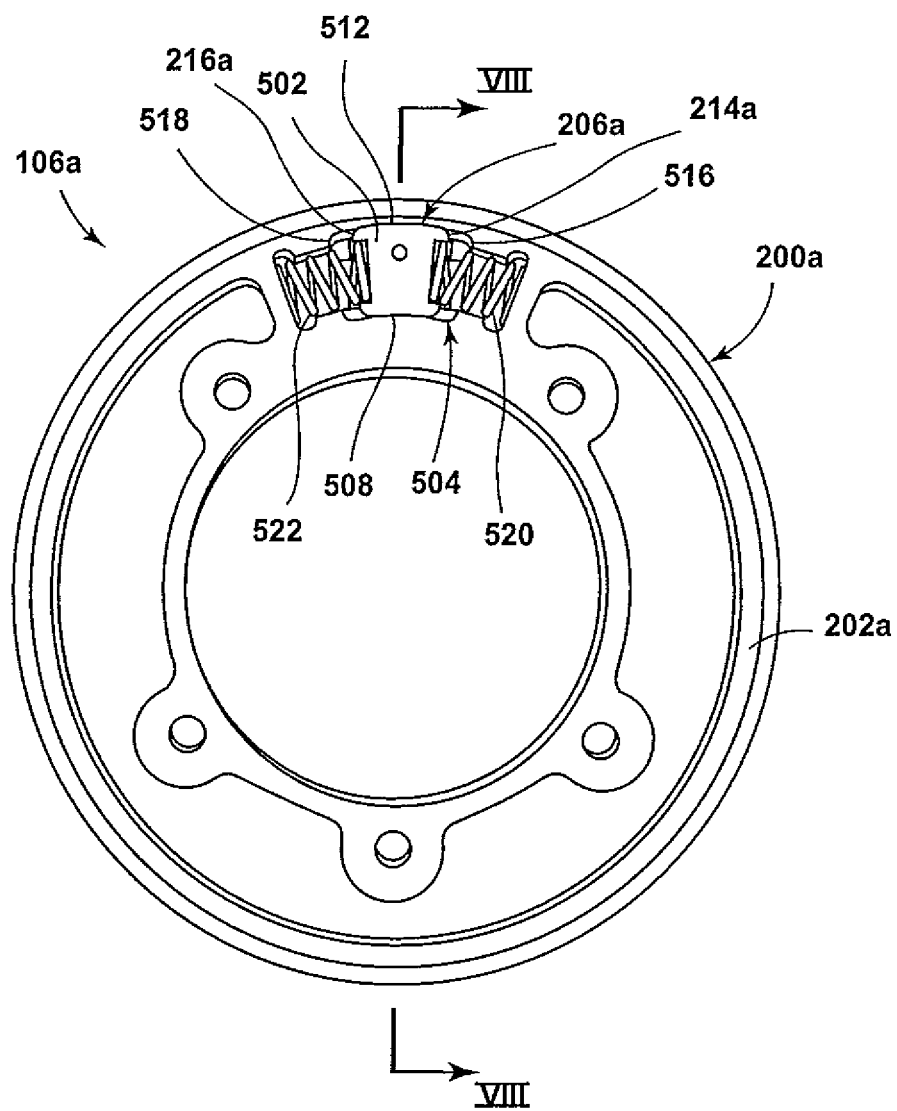
FIG. 7 is a top view of an idler member of a second rotary joint with a multi-stage rotary overtravel stop according to the invention.
Figure 8:
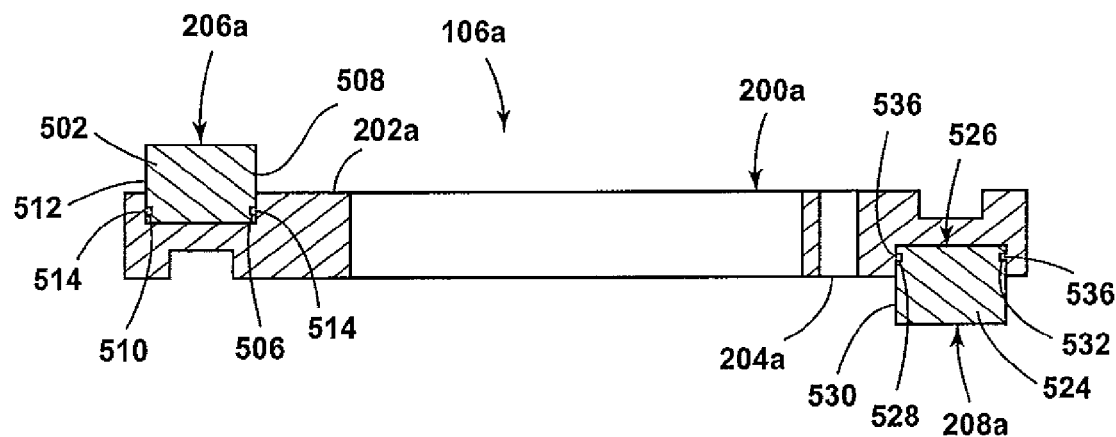
FIG. 8 is a cross-sectional view of the idler member of the second rotary joint taken along substantially line VIII-VIII of FIG. 7.

As illustrated in FIGS. 7 and 8, the third abutment 206a is a block 502 configured to angularly slide within a third abutment slot 504. The third abutment 206a includes an inner groove 506 on a radially inward facing surface 508 and an outer groove 510 on a radially outward facing surface 512. A pair of aligned tongues 514 extend radially into the third abutment slot 504 and into the inner groove 506 and the outer groove 510 to allow the third abutment 206a to slide within and be retained within the third abutment slot 504. The third alignment slot 504 has a first side end wall 516 and a second side end wall 518, with the first side end wall 516 and the second side end wall 518 limiting angular movement of the third abutment 206a relative to the disc 200a. A first side spring 520 extends through an opening in the first side end wall 516 to contact a third abutment first contact edge 214a and a second side spring 522 extends through an opening in the second side end wall 518 to contact a third abutment second contact edge 216a. The first side spring 520 and the second side spring 522 damp the impact of the third abutment 206a with the first abutment 112.

In the illustrated embodiment, a bottom view of the idler member 106a is a mirror image of the idler member 106 shown in FIG. 7. Accordingly, the fourth abutment 208a is a block 524 configured to angularly slide within a fourth abutment slot 526. The fourth abutment 208a includes an inner groove 528 on a radially inward facing surface 530 and an outer groove 532 on a radially outward facing surface 534. A pair of aligned tongues 536 extend radially into the fourth abutment slot 526 and into the inner groove 528 and the outer groove 532 to allow the fourth abutment 208a to slide within and be retained within the fourth abutment slot 526. The fourth abutment slot 526 includes end walls for limiting angular movement of the fourth abutment 208a relative to the disc 200a and springs to damp the impact of the fourth abutment 208a with the second abutment 140. It is contemplated that any other spring and/or damping member or system could be substituted for any of the springs (e.g., dashpot, elastomer, gel pack). Moreover, any of the abutments could have similar springs or damping members for damping impacts of abutments with other abutments.

Figure 9:
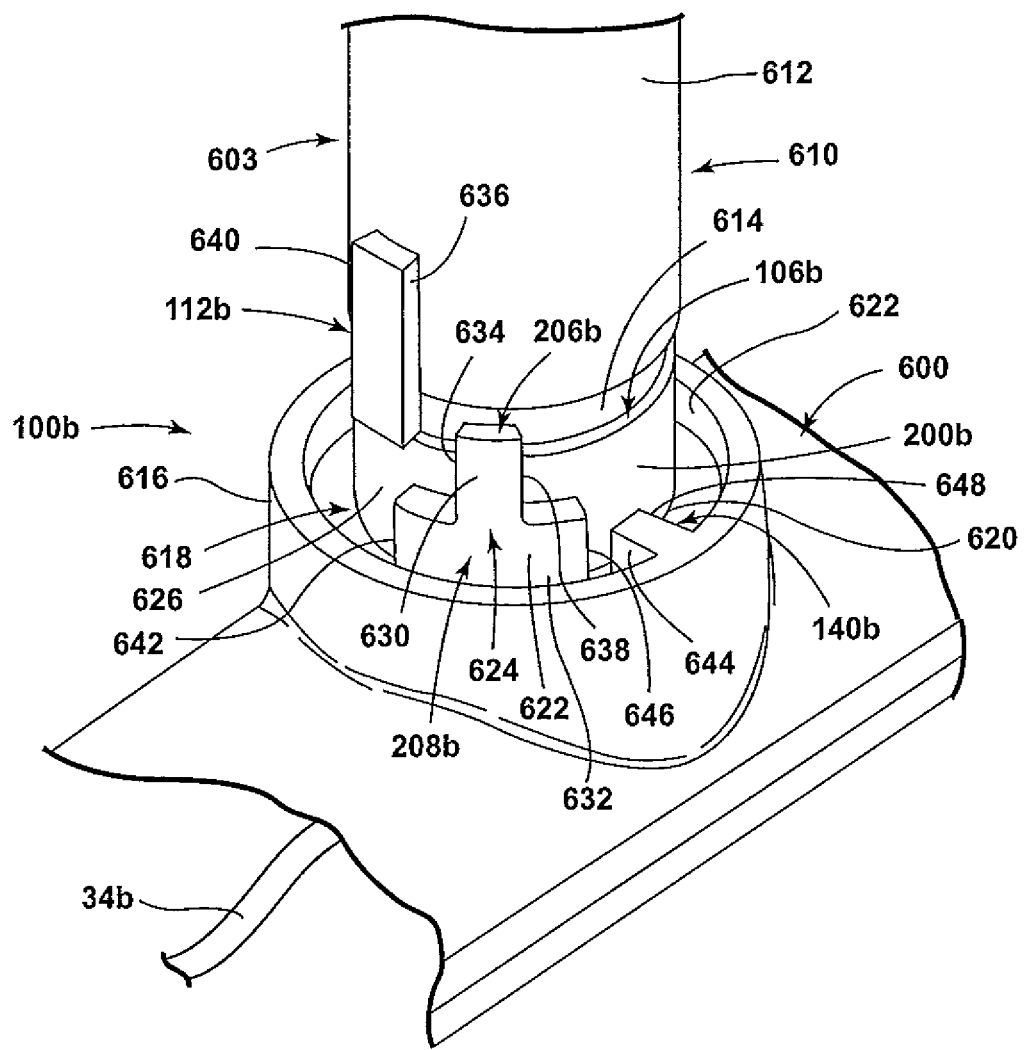
FIG. 9 is a perspective view of a third rotary joint with a multi-stage rotary overtravel stop according to the invention.

The reference numeral 100b (FIG. 9) generally designates another embodiment of the present invention, which includes a second embodiment for the rotary joint. The second embodiment of the rotary joint 100b is illustrated as being used with the second arm assembly 20. The second embodiment of the rotary joint 100b is illustrated as being located adjacent the wrist joint 32 of the second arm assembly 20. The rotary joint 100b is provided between an extension 603 extending from the wrist joint 32 and a monitor holding bracket 600 holding the monitor 12b. The monitor holding bracket 600 holds the monitor 12b and allows the monitor 12b to pivot about the bracket 600 at end points 602 of the monitor holding bracket 600. A handle 604 connected to the monitor 12b is used to selectively move the monitor 12b. In FIG. 9, a sleeve 606 located over the extension 603 and portions of the monitor holding bracket 600 are removed for clarity.

In the illustrated example, the extension 603 includes a support cylinder 610 connected to the wrist joint 32. The support cylinder 610 includes an upper larger cylindrical portion 612. A lower smaller cylindrical portion 614 extends from the monitor holding bracket 600 and into the upper larger cylindrical portion 612. It is contemplated that the lower smaller cylindrical portion 614 could be rotatable relative to the upper larger cylindrical portion 612 or could be rotatably connected to the monitor holding bracket 600 to allow the monitor holding bracket 600 to rotate relative to the extension 603. A first abutment 112b in the form of a rectangular block is connected to the upper larger cylindrical portion 612 and extends downwardly therefrom over and radially spaced from the lower smaller cylindrical portion 614.

The illustrated monitor holding bracket 600 is rotatably connected to the extension 603. The monitor holding bracket 600 includes an upwardly extending cylinder 616 accepting the lower smaller cylindrical portion 614 of the support cylinder 610 of the extension 603 therein. As illustrated in FIG. 9, the upwardly extending cylinder 616 of the monitor holding bracket 600 includes a disc-shaped plate 618 extending radially inwardly below the upper larger cylindrical portion 612, with a radially inner edge 620 surrounding and being closely adjacent or abutting the lower smaller cylindrical portion 614 of the support cylinder 610. A second abutment 140b in a form of a rectangular block extends radially inwardly from an inner cylindrical surface 622 of the upwardly extending cylinder 616 and axially from the disc-shaped plate 618 towards the upper larger cylindrical portion 612 of the support cylinder 610 of the extension 603.

Figure 10:
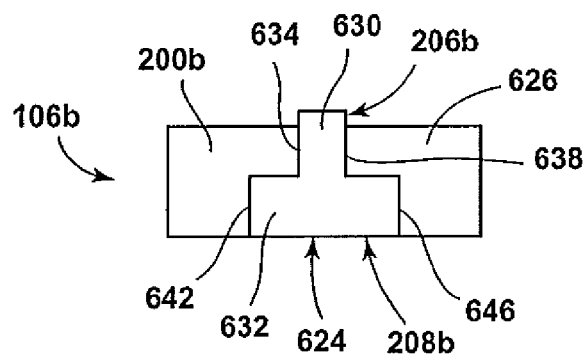
FIG. 10 is a side view of the third rotary joint with the multi-stage rotary overtravel stop according to the invention.

In the illustrated example, an idler member 106b (FIG. 10) surrounds the lower smaller cylindrical portion 614 of the support cylinder 610 of the extension 603. The idler member 106b is disc-shaped and includes a disc 200b in the form of a ring and includes an inverted T-shaped abutment member 624 extending radially outwardly from an outer cylindrical surface 626 of the idler member 106b. The disc 200b is configured to freely rotate about the lower smaller cylindrical portion 614 of the support cylinder 610 of the extension 603 while riding on the disc-shaped plate 618.

The illustrated idler member 106b limits rotation of the extension 603 relative to the monitor holding bracket 600. The inverted T-shaped abutment member 624 of the idler member 106b includes an upper leg 630 defining a third abutment 206b and a foot 632 defining a fourth abutment 208b. The third abutment 206b includes a third abutment first side edge 634 configured to abut a first abutment first side edge 636 of the first abutment 112b during rotation of the idler member 106b in a first direction and a third abutment second side edge 638 configured to abut a first abutment second side edge 640 of the first abutment 112b during rotation of the idler member 106b in a second direction opposite to the first direction, thereby limiting rotation of the idler member 106b relative to the extension 603. The fourth abutment 208b includes a fourth abutment first side edge 642 configured to abut a second abutment first side edge 644 of the second abutment 140b during rotation of the idler member 106b in a first direction and a fourth abutment second side edge 646 configured to abut a second abutment second side edge 648 of the second abutment 140b during rotation of the idler member 106b in a second direction, thereby limiting rotation of the idler member 106b relative to the monitor holding bracket 600.

In the illustrated example, the idler member 106b of the second embodiment of the rotary joint 100b limits rotation of the monitor 12b relative to the second arm assembly 20. The idler member 106b allows more than 360° of rotation, but not unlimited rotation, thereby preventing potentially damaging twisting to the at least one conduit 34b extending through the second arm assembly 20 and the monitor holding bracket 600 to the monitor 12b.

Figure 11:
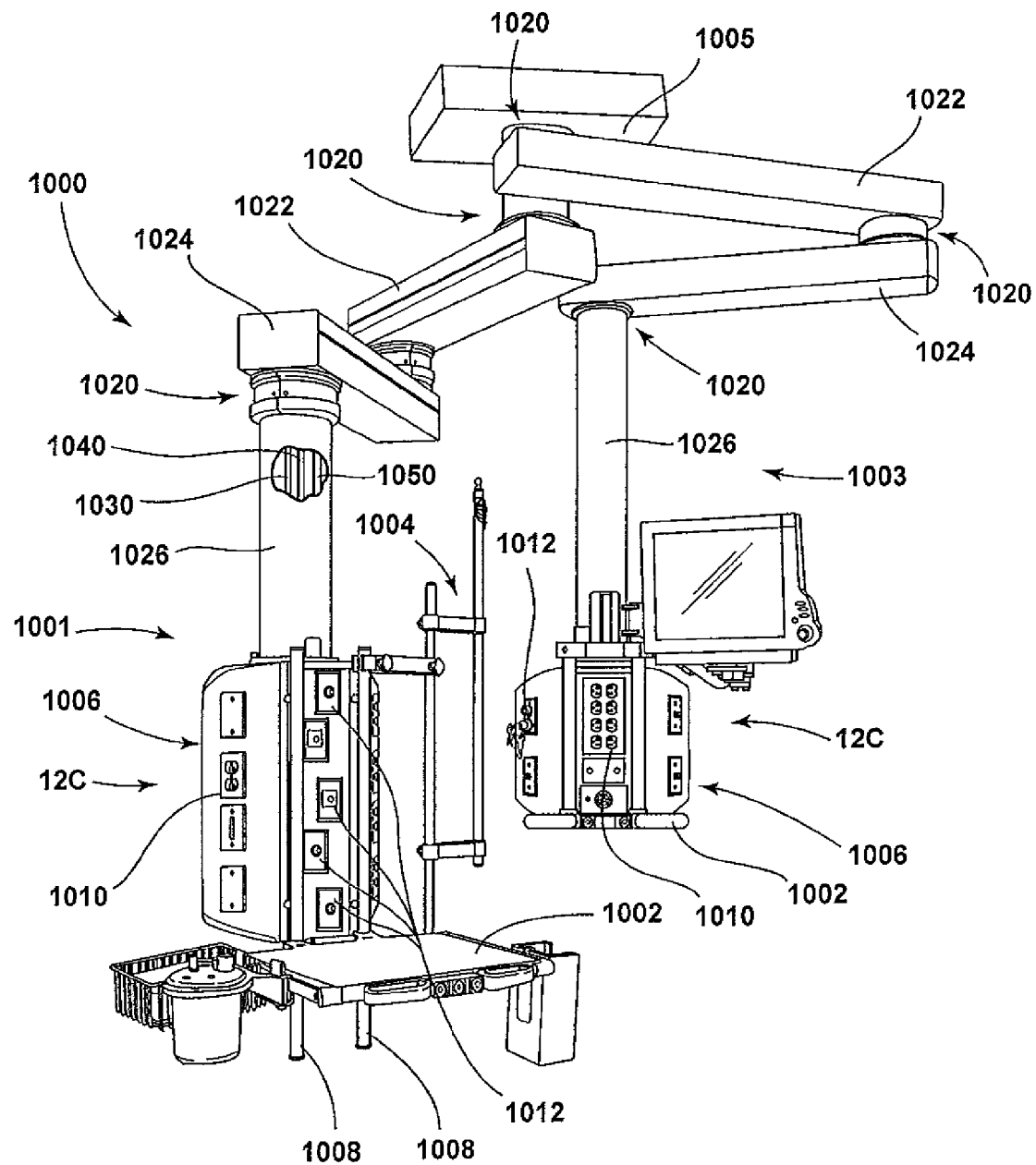
FIG. 11 is a perspective view of a second medical device assembly according to the invention.

FIG. 11 illustrates a second medical device assembly 1000 according to the invention. The second medical device assembly 1000 includes a base 1005 connected to a ceiling, with the base 1005 having a first arm assembly 1001 and a second arm assembly 1003 connected thereto that can be selectively moved and positioned to allow for a person to position respective medical units 12c. The first arm assembly 1001 and the second arm assembly 1003 each include a first arm 1022 rotatably connected to the base 1005 at a rotary joint 1020, a second arm 1024 rotatably connected to the first arm 1022 at a rotary joint 1020 and a post 1026 rotatably connected to the second arm 1026 at a rotary joint 1020. At least one conduit (e.g., electrical power cables 1030, gas lines 1040 and data cables 1050) pass from the base 1005, through the first arm assembly 1001 and the second arm assembly 1003 and to the medical units 12c to provide electricity, data and/or gas to the medical units 12c. All of the rotary joints 1020 can comprise the rotary joints 100 and 100b of the present invention as described above to allow the elements on each side of the rotary joint 1020 to have a maximum angular displacement that is greater than 360°.

The medical units 12c are utilized to provide electricity, data and/or gas to support the functioning of various types of medical equipment utilized in a patient care area. More specifically, the medical units 12c of the second medical device assembly 1000 each include a service head 1006 connected to the post 1026. Each service head 1006, in the illustrated embodiment, includes electrical outputs or outlets 1010 connected to the electrical power cables 1030 and/or other outputs or outlets 1012 for video or data communication connected to the electrical data cables 1050 or gas outputs for supplying gas from the gas lines 1040. In the illustrated embodiment, the service heads 1006 include a pair of rods or rails 1008 which support at least one adjustable shelf 1002. The adjustable shelf 1002 can support medical apparatus such as a fluid pump (not shown) and/or an IV support pole system 1004. Such a service head arrangement is the FLEXIS® system as sold by Stryker Corporation of Kalamazoo, Mich.

Although the present invention has been described with reference to specific exemplary embodiments, it will be recognized that the invention is not limited to the embodiments described, but can be practiced with modification and alteration within the spirit and scope of the appended claims. For example, the rotary joints 100 and 100b of the present invention could be used in any joint in any application outside of the medical field for allowing more than 360° of rotation, but not unlimited rotation. Moreover, even though the at least one conduit 34 is illustrated as extending through the arm assemblies and through the idler members, it is contemplated that the at least one conduit 34 could go around the idler member and/or possibly around the arms, brackets and/or joints. Accordingly, the specification and drawings are to be regarded in an illustrative sense rather than a restrictive sense.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A rotary joint for use in a medical application comprising:
   a first linkage having a first abutment;
   a second linkage rotatably connected to the first linkage, the second linkage having a second abutment;
   at least one idler member having a third abutment at a top side thereof and a fourth abutment at a bottom side thereof; and
   at least one conduit extending through the first linkage and the second linkage;
   the first linkage having at least one connector being rotatably fixed to the second linkage for allowing the first linkage to rotate relative to the second linkage; and
   the at least one idler member being free to rotate relative to the first linkage and the second linkage until the first abutment of the first linkage abuts the third abutment of the at least one idler member and until the second abutment of the second linkage abuts the fourth abutment of the at least one idler member;
   wherein the first linkage is able to rotate relative to the second linkage at a maximum angular displacement that is greater than 360°;
   wherein the first linkage, the second linkage and the at least one idler member all rotate relative to each other about a single axis; and
   wherein the second linkage includes a shelving system.

2. The rotary joint of claim 1, wherein:
   a maximum angular distance of rotation of the first linkage relative to the second linkage is less than 720°, with the first abutment, the second abutment, the third abutment and the fourth abutment preventing the first linkage from rotating the maximum angular displacement of more than 720° relative to the second linkage; and
   the maximum angular distance of rotation of the first linkage relative to the second linkage is calculated as follows:

$$720° - A_1 - A_2 - A_3 - A_4,$$

with $A_1$ being equal to a first angular width of the first abutment, $A_2$ being equal to a second angular width of the second abutment, $A_3$ being equal to a third angular width of the third abutment, and $A_4$ being equal to a fourth angular width of the fourth abutment.

3. The rotary joint of claim 1, wherein:
   the at least one idler member comprises a flat disc with an open center in a middle thereof, a flat top surface and a flat bottom surface;
   the third abutment extends axially from the flat top surface of the flat disc; and
   the fourth abutment extends axially from the flat bottom surface of the flat disc.

4. The rotary joint of claim 1, wherein:
   the at least one idler member is disc-shaped.

5. The rotary joint of claim 1, wherein:
   the at least one idler member has an open center.

6. The rotary joint of claim 1, wherein:
the at least one idler member comprises a plurality of idler members.

7. The rotary joint of claim 1, wherein:
the at least one conduit comprises electrical cabling.

8. A rotary joint for use in a medical application comprising:
a first linkage having a first abutment;
a second linkage rotatably connected to the first linkage, the second linkage having a second abutment;
at least one idler member having a third abutment at a top side thereof and a fourth abutment at a bottom side thereof; and
at least one conduit extending through the first linkage and the second linkage;
the first linkage having at least one connector being rotatably fixed to the second linkage for allowing the first linkage to rotate relative to the second linkage; and
the at least one idler member being free to rotate relative to the first linkage and the second linkage until the first abutment of the first linkage abuts the third abutment of the at least one idler member and until the second abutment of the second linkage abuts the fourth abutment of the at least one idler member;
wherein the first linkage is able to rotate relative to the second linkage at a maximum angular displacement that is greater than 360°;
wherein the first linkage, the second linkage and the at least one idler member all rotate relative to each other about a single axis;
wherein the at least one idler member comprises a flat disc with an open center in a middle thereof, a top surface and a bottom surface;
wherein the third abutment rests in a top arcuate channel in the top surface of the flat disc and extends axially from the top surface of the flat disc;
wherein the third abutment is configured to slide angularly within the top arcuate channel;
wherein the fourth abutment rests in a bottom arcuate channel in the bottom surface of the flat disc and extends axially from the bottom surface of the flat disc;
wherein the fourth abutment is configured to slide angularly within the bottom arcuate channel;
wherein at least one top damping member abuts a radial face of the third abutment to damp movement of the third abutment within the top arcuate channel; and
wherein at least one bottom damping member abuts a radial face of the fourth abutment to damp movement of the fourth abutment within the bottom arcuate channel.

9. The rotary joint of claim 8, wherein:
the second linkage is a camera.

10. The rotary joint of claim 8, wherein:
the second linkage includes a monitor.

11. A rotary joint for use in a medical application comprising:
a first linkage having a first abutment;
a second linkage rotatably connected to the first linkage, the second linkage having a second abutment;
at least one idler member having a third abutment at a top side thereof and a fourth abutment at a bottom side thereof; and
at least one conduit extending through the first linkage and the second linkage;
the first linkage having at least one connector being rotatably fixed to the second linkage for allowing the first linkage to rotate relative to the second linkage; and
the at least one idler member being free to rotate relative to the first linkage and the second linkage until the first abutment of the first linkage abuts the third abutment of the at least one idler member and until the second abutment of the second linkage abuts the fourth abutment of the at least one idler member;
wherein the first linkage is able to rotate relative to the second linkage at a maximum angular displacement that is greater than 360°;
wherein the first linkage, the second linkage and the at least one idler member all rotate relative to each other about a single axis;
wherein the at least one idler member comprises a ring with a cylindrical outer face and a T-shaped member extending radially from the cylindrical outer face; and
wherein the T-shaped member comprising the third abutment on a leg thereof and the fourth abutment on a cross-member thereof.

12. A rotary joint for use in a medical application comprising:
a first linkage having a first abutment;
a second linkage rotatably connected to the first linkage, the second linkage having a second abutment;
at least one idler member having a third abutment at a top side thereof and a fourth abutment at a bottom side thereof; and
at least one conduit extending through the first linkage and the second linkage;
the first linkage having at least one connector being rotatably fixed to the second linkage for allowing the first linkage to rotate relative to the second linkage; and
the at least one idler member being free to rotate relative to the first linkage and the second linkage until the first abutment of the first linkage abuts the third abutment of the at least one idler member and until the second abutment of the second linkage abuts the fourth abutment of the at least one idler member;
wherein the first linkage is able to rotate relative to the second linkage at a maximum angular displacement that is greater than 360°;
wherein the first linkage, the second linkage and the at least one idler member all rotate relative to each other about a single axis; and
wherein the at least one conduit comprises gas hoses.

13. The rotary joint of claim 12, wherein:
a maximum angular distance of rotation of the first linkage relative to the second linkage is less than 720°, with the first abutment, the second abutment, the third abutment and the fourth abutment preventing the first linkage from rotating the maximum angular displacement of more than 720° relative to the second linkage; and
the maximum angular distance of rotation of the first linkage relative to the second linkage is calculated as follows:

$$720° - A_1 - A_2 - A_3 - A_4,$$

with $A_1$ being equal to a first angular width of the first abutment, $A_2$ being equal to a second angular width of the second abutment, $A_3$ being equal to a third angular width of the third abutment, and $A_4$ being equal to a fourth angular width of the fourth abutment.

14. A medical device assembly comprising:
a first member having a first abutment;
a second member rotatably connected to the first member, the second member having a second abutment;

at least one idler member having a third abutment at a top side thereof and a fourth abutment at a bottom side thereof; and at least one conduit extending through the first member and the second member;

the first member being rotatably fixed to the second member; and the at least one idler member being free to rotate relative to the first member and the second member until the first abutment of the first member abuts the third abutment of the at least one idler member and until the second abutment of the second member abuts the fourth abutment of the at least one idler member;

wherein the first member, the second member and the at least one idler member all rotate relative to each other about a single axis; and wherein the at least one conduit comprises gas hoses.

15. The medical device assembly of claim 14, wherein: the at least one idler member has a center opening.

16. The medical device assembly of claim 15, wherein: the at least one conduit extends through the center opening of the at least one idler member.

17. The medical device assembly of claim 14, wherein: the first member is able to rotate relative to the second member at a maximum angular displacement that is greater than 360°.

18. The medical device assembly of claim 14, wherein: the at least one idler member comprises a plurality of idler members.

19. The medical device assembly of claim 14, wherein: the at least one idler member comprises a flat disc with an open center in a middle thereof, a flat top surface and a flat bottom surface;

the third abutment extends axially from the flat top surface of the flat disc; and the fourth abutment extends axially from the flat bottom surface of the flat disc.

20. The medical device assembly of claim 14, wherein: the at least one idler member is disc-shaped.

21. The medical device assembly of claim 14, wherein: the at least one idler member has an open center.

22. The medical device assembly of claim 14, wherein: the at least one conduit comprises electrical cabling.

23. A medical device assembly comprising:

a first member having a first abutment;

a second member rotatably connected to the first member, the second member having a second abutment;

at least one idler member having a third abutment at a top side thereof and a fourth abutment at a bottom side thereof; and at least one conduit extending through the first member and the second member;

the first member being rotatably fixed to the second member; and the at least one idler member being free to rotate relative to the first member and the second member until the first abutment of the first member abuts the third abutment of the at least one idler member and until the second abutment of the second member abuts the fourth abutment of the at least one idler member;

wherein the first member, the second member and the at least one idler member all rotate relative to each other about a single axis; and wherein the second linkage includes a shelving system.

24. The medical device assembly of claim 23, wherein: the first member is able to rotate relative to the second member at a maximum angular displacement that is greater than 360°.

25. A medical device assembly comprising:

a first member having a first abutment;

a second member rotatably connected to the first member, the second member having a second abutment;

at least one idler member having a third abutment at a top side thereof and a fourth abutment at a bottom side thereof; and at least one conduit extending through the first member and the second member;

the first member being rotatably fixed to the second member; and the at least one idler member being free to rotate relative to the first member and the second member until the first abutment of the first member abuts the third abutment of the at least one idler member and until the second abutment of the second member abuts the fourth abutment of the at least one idler member;

wherein the first member, the second member and the at least one idler member all rotate relative to each other about a single axis;

wherein the at least one idler member comprises a flat disc with an open center in a middle thereof, a top surface and a bottom surface;

wherein the third abutment rests in a top arcuate channel in the top surface of the flat disc and extends axially from the top surface of the flat disc;

wherein the third abutment is configured to slide angularly within the top arcuate channel;

wherein the fourth abutment rests in a bottom arcuate channel in the bottom surface of the flat disc and extends axially from the bottom surface of the flat disc;

wherein the fourth abutment is configured to slide angularly within the bottom arcuate channel;

wherein at least one top damping member abuts a radial face of the third abutment to damp movement of the third abutment within the top arcuate channel; and wherein at least one bottom damping member abuts a radial face of the fourth abutment to damp movement of the fourth abutment within the bottom arcuate channel.

26. A medical device assembly comprising:

a first member having a first abutment;

a second member rotatably connected to the first member, the second member having a second abutment;

at least one idler member having a third abutment at a top side thereof and a fourth abutment at a bottom side thereof; and at least one conduit extending through the first member and the second member;

the first member being rotatably fixed to the second member; and the at least one idler member being free to rotate relative to the first member and the second member until the first abutment of the first member abuts the third abutment of the at least one idler member and until the second abutment of the second member abuts the fourth abutment of the at least one idler member;

wherein the first member, the second member and the at least one idler member all rotate relative to each other about a single axis;

wherein the at least one idler member comprises a ring with a cylindrical outer face and a T-shaped member extending radially from the cylindrical outer face; and wherein the T-shaped member comprising the third abutment on a leg thereof and the fourth abutment on a cross-member thereof.

27. The medical device assembly of claim 26, wherein:
the second linkage is a camera.

28. The medical device assembly of claim 26, wherein:
the second linkage includes a monitor.

\* \* \* \* \*